US010448982B2

(12) United States Patent
Schmidt et al.

(10) Patent No.: US 10,448,982 B2
(45) Date of Patent: Oct. 22, 2019

(54) REINFORCED CANNULATED SCREW ASSEMBLY SYSTEMS AND METHODS

(71) Applicant: CURAX SCIENTIFIC, LLC, St. Louis, MO (US)

(72) Inventors: Gary J. Schmidt, St. Louis, MO (US); A. Jamie Riley, St. Louis, MO (US); Amod P. Paranjpe, Augusta, MO (US); Gene Zamba, Valencia, CA (US)

( * ) Notice: Subject to any disclaimer, the term of this patent is extended or adjusted under 35 U.S.C. 154(b) by 813 days.

(21) Appl. No.: 14/710,172

(22) Filed: May 12, 2015

(65) Prior Publication Data
US 2015/0320464 A1 Nov. 12, 2015

Related U.S. Application Data

(60) Provisional application No. 61/992,005, filed on May 12, 2014.

(51) Int. Cl.
*A61B 17/86* (2006.01)
*A61B 17/88* (2006.01)

(52) U.S. Cl.
CPC .......... *A61B 17/863* (2013.01); *A61B 17/864* (2013.01); *A61B 17/8685* (2013.01); *A61B 17/888* (2013.01); *A61B 17/8615* (2013.01); *A61B 17/8645* (2013.01)

(58) Field of Classification Search
CPC . A61B 17/863; A61B 17/864; A61B 17/8685; A61B 17/888; A61B 17/8615; A61B 17/8645; F16B 23/0038; F16B 23/003
USPC ................. 606/304; 411/479, 356–359, 922; 433/173, 175, 172, 174, 176
See application file for complete search history.

(56) References Cited

U.S. PATENT DOCUMENTS

| | | | |
|---|---|---|---|
| 4,013,071 A * | 3/1977 | Rosenberg | A61B 17/686 411/397 |
| 5,209,753 A | 5/1993 | Biedermann et al. | |
| 5,549,431 A * | 8/1996 | Royle | B25B 13/54 411/389 |
| 6,663,656 B2 * | 12/2003 | Schmieding | A61B 17/8615 606/232 |
| 2009/0198289 A1 | 8/2009 | Manderson | |
| 2012/0095515 A1 | 4/2012 | Hamilton | |
| 2013/0211196 A1 | 8/2013 | Belson et al. | |

OTHER PUBLICATIONS

"Truss Head Break Away Screw, #8-32 thread x 1-3/4" , 20-Pack: Home Improvement." Amazon.com: Truss Head Break Away Screw, #8-32 thread x 1-3/4" , 20-Pack: Home Improvement, www.amazon.com/Truss-Break-Screw-thread-20-Pack/dp/B001FTMOOA/ref=sr_1_6?ie=UTF8&qid=1519832382&sr=8-6&keywords=breakaway%2Bscrews, accessed Feb. 28, 2018, cited as Amazon.*

* cited by examiner

*Primary Examiner* — David W Bates
*Assistant Examiner* — Marcela I Shirsat
(74) *Attorney, Agent, or Firm* — Sandberg Phoenix & von Gontard, P.C.

(57) ABSTRACT

A reinforced cannulated screw assembly includes a cannulated screw and a reinforcing rod coupled to the cannulated screw. The cannulated screw includes a channel formed therethrough that is defined by an inner wall having at least one set of grooves formed therein. The reinforcing rod is configured for insertion into the channel. The reinforcing rod includes a set of protrusions configured to engage the at least one set of grooves.

12 Claims, 9 Drawing Sheets

REINFORCED CANNULATED SCREW ASSEMBLY SYSTEMS AND METHODS

CROSS REFERENCE TO RELATED APPLICATIONS

This application claims priority to U.S. Provisional Application No. 61/992,005 filed on May 12, 2014, which is hereby incorporated by reference in its entirety.

BACKGROUND

The present disclosure relates generally to systems and methods of neutralizing a bone fracture and other orthopedic reconstruction procedures, and, more specifically, to systems and methods of utilizing a reinforced cannulated screw assembly during an orthopedic procedure.

Orthopedic procedures often demand the application of significant forces in specific ways and/or directions, or combinations thereof. The details of the injury and anatomy being treated dictate how the procedure is performed and generally do not tailor themselves to the skill of the surgeon or the ease of use of the available equipment.

One factor that contributes to a surgeon's challenges is precise placement of orthopedic or surgical screws in a patient's bone. Precise placement, location and angle, is important because the surgeon does not want to crack or weaken the bone by putting the screw too close to the edge of the bone or in a part of the bone which is too shallow.

Therefore, at least some known surgical screws have been cannulated, i.e., made with a longitudinal bore ("cannula") for a guide wire. The cannulated screw is guided into place by the guide wire. Then the screw is threaded into the bone. However, due to cannulation, such a screw is significantly weaker than a solid screw.

Cannulated screws have broad application and may need to be in place for decades while being subject to dynamic loading. Therefore, it is desirable to improve the strength of a cannulated screw. Moreover, surgical screws may at some point need to be removed. For example, screws used in children may need to be removed subsequently in view of impending bone growth, or screws that are later determined to be improperly placed, break, cause pain, irritation, infection or other problems usually need to be removed. It is good medical practice to ensure that any screws and other fixation implants are capable of being removed if necessary. Additionally, stripping of threads on the screw may occur either during insertion or removal. Removal of a stripped screw may be more difficult.

Accordingly, a system for reinforcing a cannulated screw and/or a system that eliminates or minimizes the chances of stripping of the cannulated screw and enables easy removal of the cannulated screw is desirable.

BRIEF DESCRIPTION

In one aspect, a reinforced cannulated screw assembly is provided. The reinforced cannulated screw assembly includes a cannulated screw and a reinforcing rod coupled to the cannulated screw. The cannulated screw includes an inner wall defining a channel therethrough. The inner wall includes at least one set of grooves formed therein. The reinforcing rod is configured for insertion into the channel. The reinforcing rod includes a set of protrusions configured to engage the at least one set of grooves.

In another aspect, a reinforced cannulated screw system is provided. The reinforced cannulated screw system includes a reinforced cannulated screw assembly including a cannulated screw and a reinforcing rod coupled to the cannulated screw. The cannulated screw includes an inner wall defining a channel therethrough. The inner wall includes at least one set of grooves formed therein. The reinforcing rod is configured for insertion into the channel. The reinforcing rod includes a set of protrusions configured to engage the at least one set of grooves. The reinforced cannulated screw system also includes a torque tool configured to engage at least one of the cannulated screw and the reinforcing rod to facilitate insertion of the reinforced cannulated screw assembly into a substrate.

In yet another aspect, a method of using a reinforced cannulated screw assembly is provided. The method includes inserting a cannulated screw into a substrate. The cannulated screw includes an inner wall defining a channel formed therethrough. The inner wall includes at least one set of grooves formed therein. The method also includes inserting a reinforcing rod into the channel. The reinforcing rod includes a set of protrusions configured to engage the at least one set of grooves. The reinforcing rod is then rotated with respect to the cannulated screw such that the plurality of protrusions engage at least one set of grooves.

DETAILED DESCRIPTION

Figure 1:
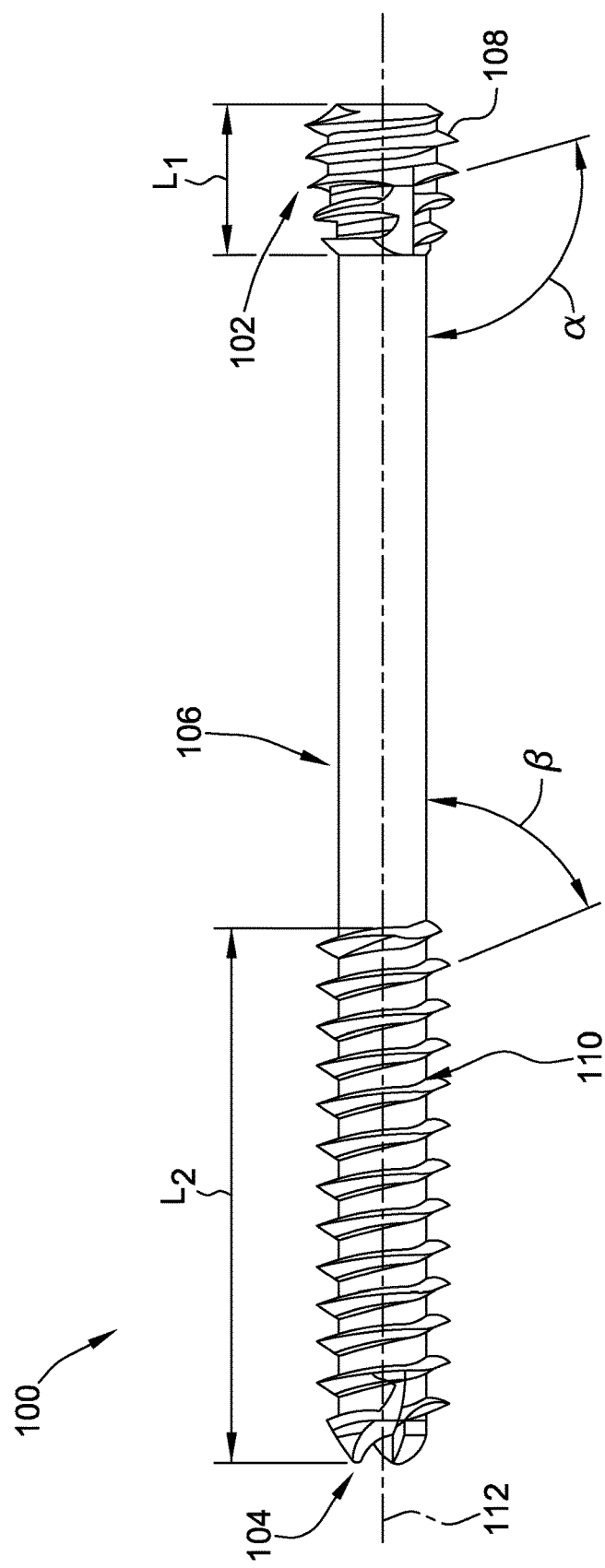
FIG. 1 is a side view of an exemplary cannulated screw.
Figure 2:
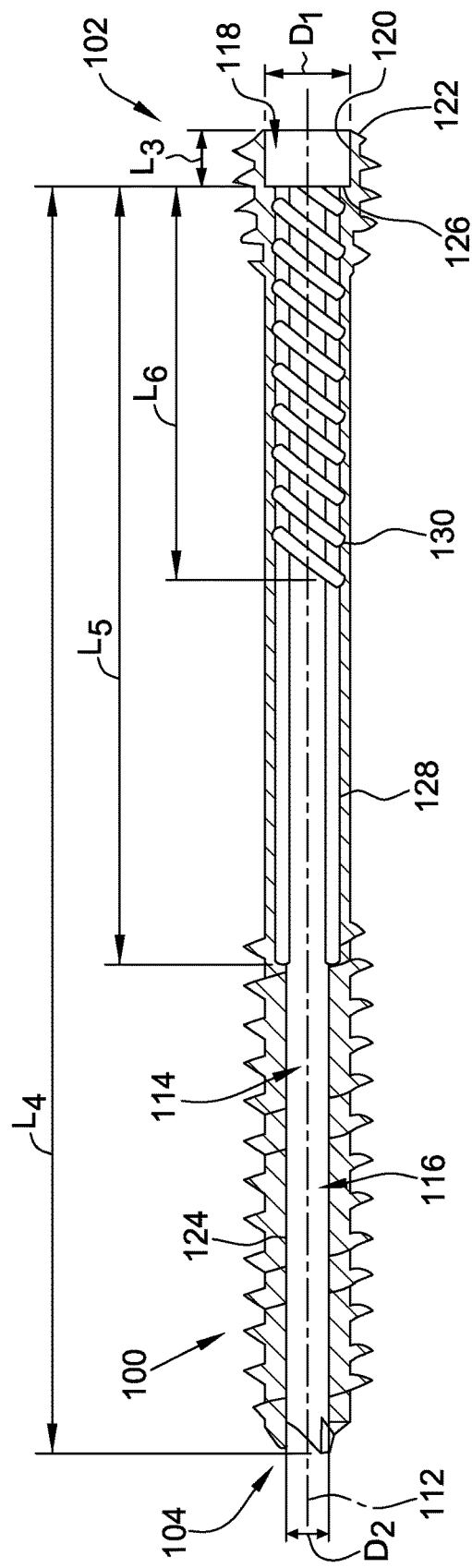
FIG. 2 is a cross-sectional view of the cannulated screw shown in FIG. 1.
Figure 3:
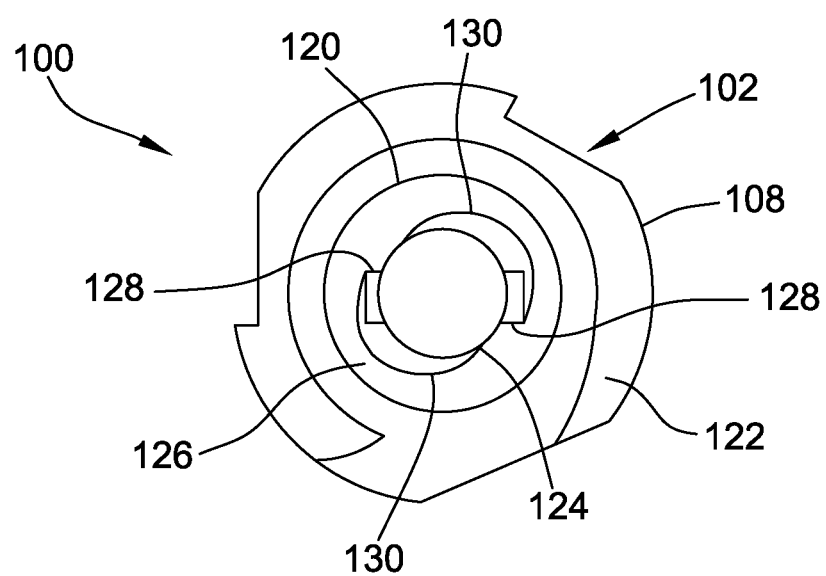
FIG. 3 is a top view of the cannulated screw shown in FIG. 1.

FIG. 1 illustrates a side view of an exemplary cannulated surgical screw 100, FIG. 2 is a cross-sectional view of screw 100, and FIG. 3 is a top view of screw 100. In the exemplary embodiment, screw 100 includes a first end, or head 102, an opposite second end, or tip 104, and a body portion 106 extending therebetween. As described in further detail below, tip 104 is configured to be inserted into a patient during surgery and head 102 is engaged by a tool to rotate screw 100 and complete insertion.

In the exemplary embodiment, screw 100 includes at least one set of external threads. More specifically, screw 100 includes a first set of threads 108 proximate head 102 and a second set of threads 110 proximate tip 104. Threads 108 extend along body 106 a first length L1 that is shorter than a second length L2 of threads 110. Further, threads 108 include a first pitch angle α with respect to a longitudinal axis 112, and threads 110 includes a second pitch axis β that is less than pitch angle α. As such, threads 108 and 110 compress any bone portions joined by screw 100. Alternatively, screw 100 may not include threads 108 and only includes threads 100 proximate tip 104. Generally, screw 100 may be any type of cannulated screw used in any type of bone fragment fixation or other surgical procedure.

As shown in FIG. 2, screw 100 includes a channel 114 defined therethrough that extends between head 102 and tip 104 along axis 112. More specifically, channel 114 includes a body portion 116 and a counter-bore 118. Counter-bore 118 is defined by a substantially cylindrical inner wall 120 that extends a third length L3 into body 106 from an outer radial surface 122 of screw 100 and that includes a first diameter D1. Similarly, channel body 116 is defined by a substantially cylindrical inner wall 124 that extends a fourth length L4 from an inner radial surface 126 of counter-bore 118 and includes a second diameter D2 that is smaller that first diameter D1.

In the exemplary embodiment, screw 100 includes a first set of grooves 128 formed in inner wall 124. More specifically, grooves 128 include a pair of oppositely-oriented grooves formed in wall 124 that extend a fifth length L5 from inner radial surface 126 along channel body 116. Grooves 128 are substantially straight, that is, parallel to longitudinal axis 112. As described in further detail below, grooves 128 are configured to receive a tool that applies torque to screw 100 to drive screw 100 into the patient's bone.

Screw 100 also includes a second set of grooves 130 formed in inner wall 124. More specifically, grooves 130 include a pair of symmetrical grooves formed in wall 124 that extend a sixth length L6 from inner radial surface 126 along channel body 116. Grooves 130 are helical in shape such that grooves 130 are spirally wound around channel body 116, as best seen in FIG. 2. As described in further detail below, grooves 130 are configured to receive protrusions formed on a reinforcing rod as it is inserted into channel 114.

In the exemplary embodiment, helical grooves 130 intersect axial grooves 128 at least one time over a predetermined length of channel body 116. Further, helical grooves 130 wind around channel body 116 such that at least a portion of grooves 128 and 130 overlap along channel body 116. Additionally, axial grooves 128 are oriented approximately 90 degrees from helical grooves 130 on radial surface 126, as best shown in FIG. 3, to facilitate insertion of the tool and the reinforcing rods at different orientations. Alternatively, axial grooves 128 are aligned with helical grooves 130 on radial surface 126. In the exemplary embodiment, axial grooves 128 extend a distance into inner wall 124 that is shorter than the distance helical grooves 130 extend into inner wall 124. As such, helical grooves 130 are deeper than axial grooves 128, and accordingly, the reinforcing rod cannot be removed without rotation, as described in further detail below.

Figure 4:
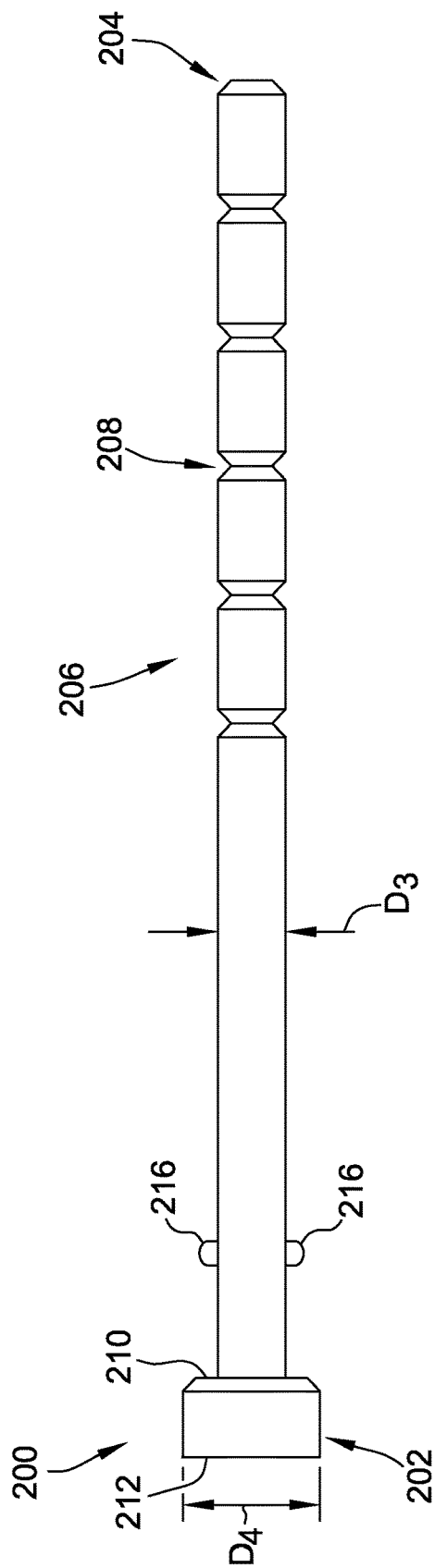
FIG. 4 is a side view of an exemplary reinforcing rod that may be used with the cannulated screw shown in FIG. 1.
Figure 5:
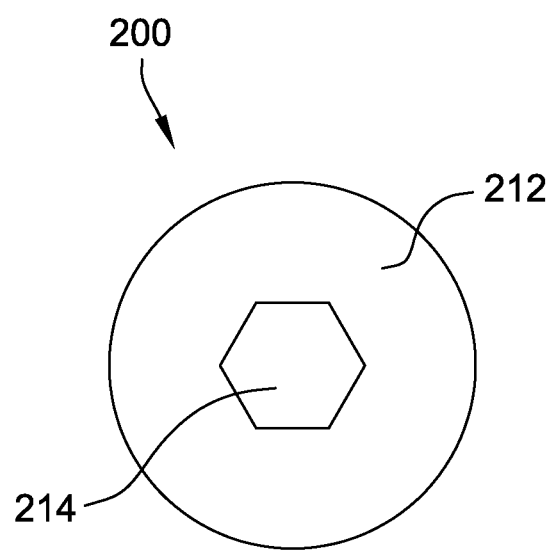
FIG. 5 is a top view of an exemplary reinforcing rod shown in FIG. 4.
Figure 6:
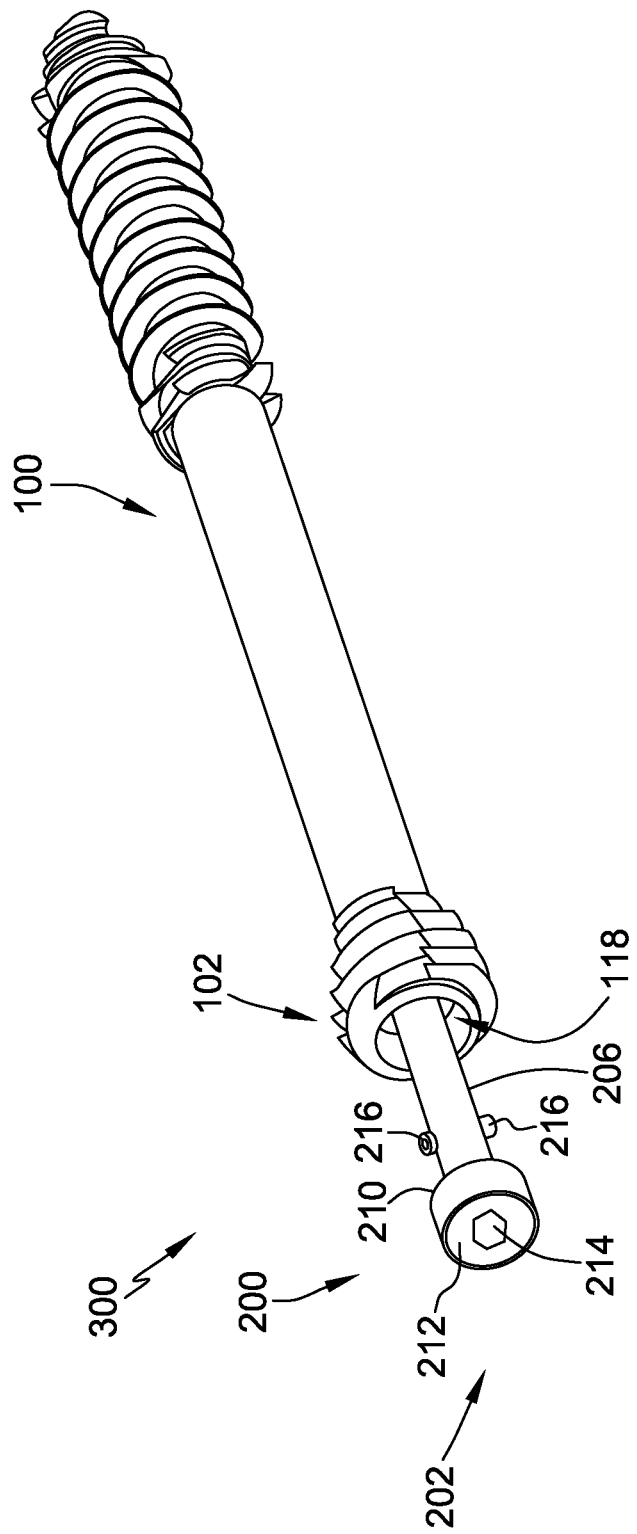
FIG. 6 is a perspective view of the reinforcing rod partially inserted into the cannulated screw.

FIG. 4 is a side view of reinforcing rod 200 that may be used with cannulated screw 100 (shown in FIG. 1), FIG. 5 is a top view of rod 200, and FIG. 6 is a perspective view of reinforcing rod 200 partially inserted into cannulated screw 100. The combination of screw 100 and rod 200 form a reinforced cannulated screw assembly 300. In the exemplary embodiment, rod 200 includes a first end, or head 202, an opposite second end, or tip 204, and a body portion 206 extending therebetween. As described in further detail below, tip 204 is configured to be inserted into channel body 116 of screw 100 and head 102 is configured to be seated within screw counter-bore 118. As such, when rod 200 is fully inserted within screw 100, rod 200 increases the overall strength of screw 100 such that the resulting strength of screw 100 is comparable to the strength of a solid screw.

In the exemplary embodiment, rod 200 includes at least one length determination feature 208 that enables a surgeon to select a length of rod 200 that can be accommodated within a particular screw 100. More specifically, rod 200 includes a plurality of features 208 axially spaced along a length of body portion 206. In the exemplary embodiment, features 208 include a plurality of circumferential grooves formed in rod body 206. Alternatively, features 208 are a plurality of score lines. Generally, length determination features 208 are any feature that indicates a predetermined length to the surgeon and enables the surgeon to select the length of rod 200. For example, screw 100 may be manufactured in a variety of different lengths for use in different procedures, and rod 200 may be manufactured in a single length that includes length determination features 208 such that the surgeon can reduce the overall length of rod 200 to correspond to a length of the selected screw. Length determination features 208 may be formed on rod 200 to correspond to known common screw lengths.

Rod body 206 includes a third diameter D3 that is slightly smaller than second diameter D2 of channel body 116 to enable insertion of rod body 206 into channel body 116. Similarly, rod head 202 includes a fourth diameter D4 that is slightly smaller than first diameter D1 of counter-bore 118 to enable insertion of rod head 202 into counter-bore 118. When rod 200 is inserted into screw 100, as shown in FIG. 6, a radial surface 210 of rod head 202 contacts radial surface 126 of screw 100 such that rod 200 is prevented from further insertion. Surfaces 210 and 126 may include a bevel or chamfer to facilitate seating of rod 200 and screw 100. Similarly, tip 204 includes a bevel or is rounded to facilitate entry of tip 204 into channel 114. In the exemplary embodiment, when rod 200 is fully inserted into screw 100, an end surface 212 of rod head 202 is substantially flush with outer surface 122 of screw 100. Alternatively, rod head 202 may be seated slightly within counter-bore 118 such that surfaces 212 and 122 are not flush. End surface 212 also includes a recess 214 that receives a tool inserted by the surgeon to enable rotation of rod 200. In one embodiment, recess 214 is hexagonal in shape, although other shapes of recess 214 are contemplated.

In the exemplary embodiment, rod 200 also includes a pair of protrusions 216 that extend radially outward from rod body 206 proximate rod head 202. Protrusions 216 are configured to engage helical grooves 130 of screw 100 to enable insertion of rod 200 into screw 100 by rotation of rod 200. As such, helical grooves 130 and protrusions 216 act as a worm gear that enables rod 200 to be smoothly inserted into channel 114 of screw 100 while reducing the occurrence of stripping grooves 130 or protrusions 216 during insertion or removal or rod 200. As described above, axial grooves 128 extend a distance into inner wall 124 that is shorter that the distance helical grooves 130 extend into inner wall 124. As such, helical grooves 130 are deeper than axial grooves 128 and the reinforcing rod cannot be removed without rotation. For example, the deeper helical grooves 130 ensure alignment of protrusions 216 with grooves 130 and prevent the surgeon from attempting insertion of protrusions 216 into shallower axial grooves 128. Further, once the surgeon seats rod 200 into screw 100, the difference in the depth of grooves 128 and 130 prevent removal of rod 200 even when protrusions 216 are aligned with axial grooves 128. That is, rod 200 is removable via rotation and cannot be removed with a purely axial force.

Figure 7:
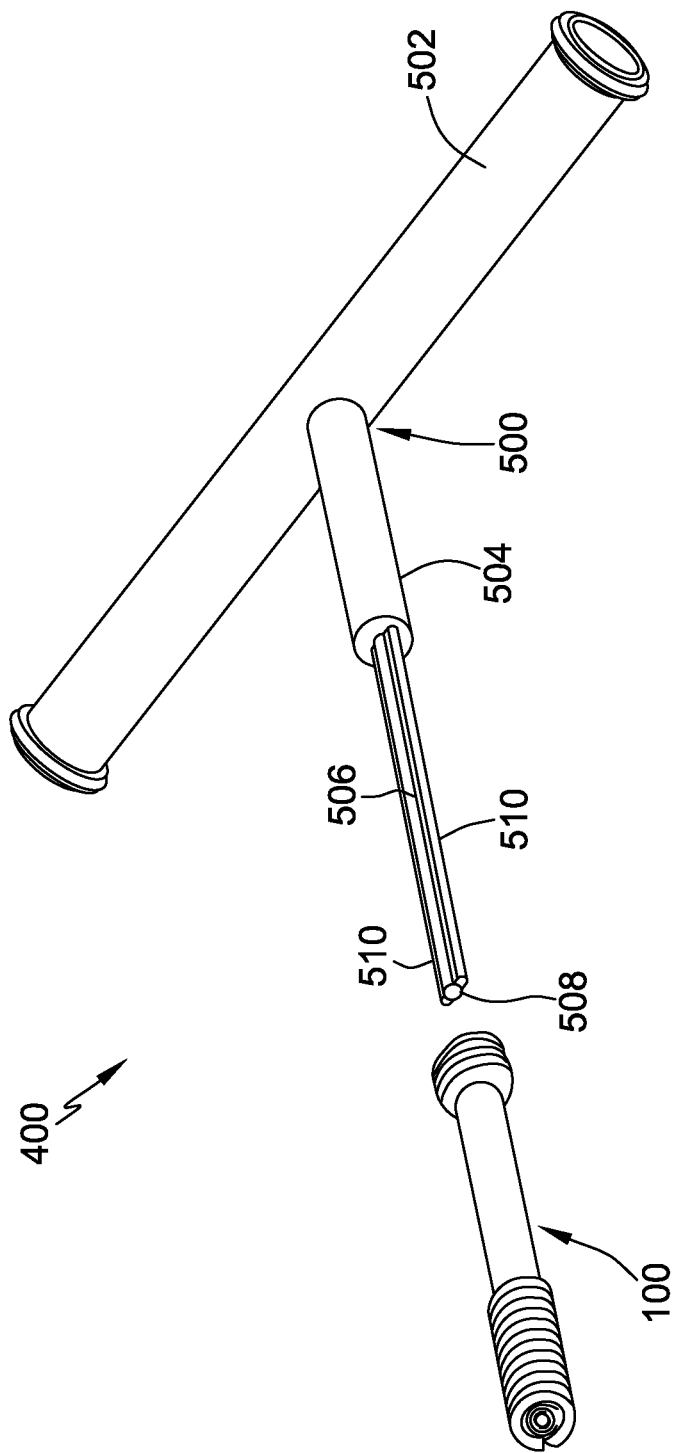
FIG. 7 is a perspective view of a torque tool arranged for engagement with the cannulated screw shown in FIG. 1.

FIG. 7 is a perspective view of a portion of a reinforced cannulated screw system 400 illustrating a torque tool 500 arranged for engagement with cannulated screw 100. Tool 500 includes a handle 502, a shaft 504 coupled to handle 502, and an engaging portion 506 extending from shaft 504. Engaging portion 506 includes a tip 508 and a pair of symmetrical flanges 510 that extend axially between shaft 504 and tip 508. In the exemplary embodiment, flanges 510 are oppositely-oriented on engaging portion 506 and are shaped to correspond with axial grooves 128 in screw 100 to enable insertion of tool engaging portion 506 into screw grooves 128. In use, engaging portion 506 is inserted into screw 100 a distance of L%, which is as deeply as axial grooves 128 permit. The surgeon may then rotate tool 500 to torque screw 100 along most if not substantially all of the length of screw 100, thus sharply reducing the chance of stripping and/or slipping and making both the insertion and removal of screw 100 easier and more reliable.

Figure 8:
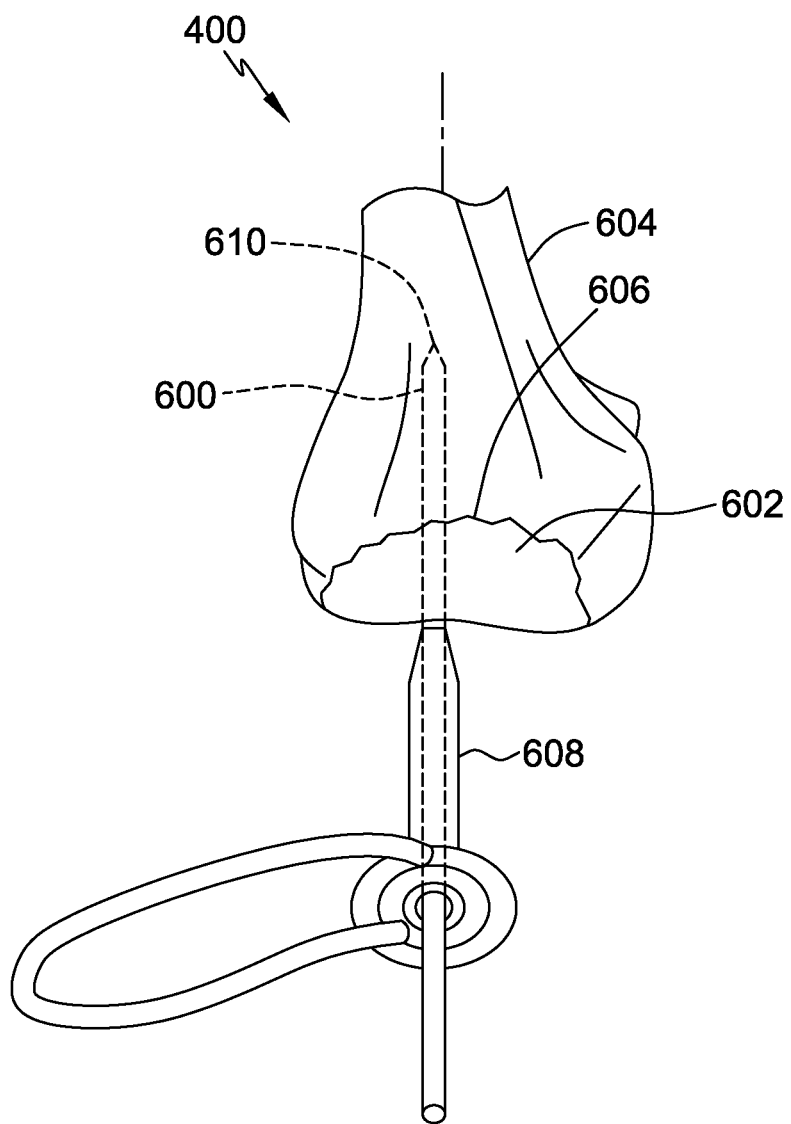
FIG. 8 is a perspective view of a portion of an exemplary cannulated screw system at a work site illustrating insertion of a guide wire into two portions of bone.
Figure 9:
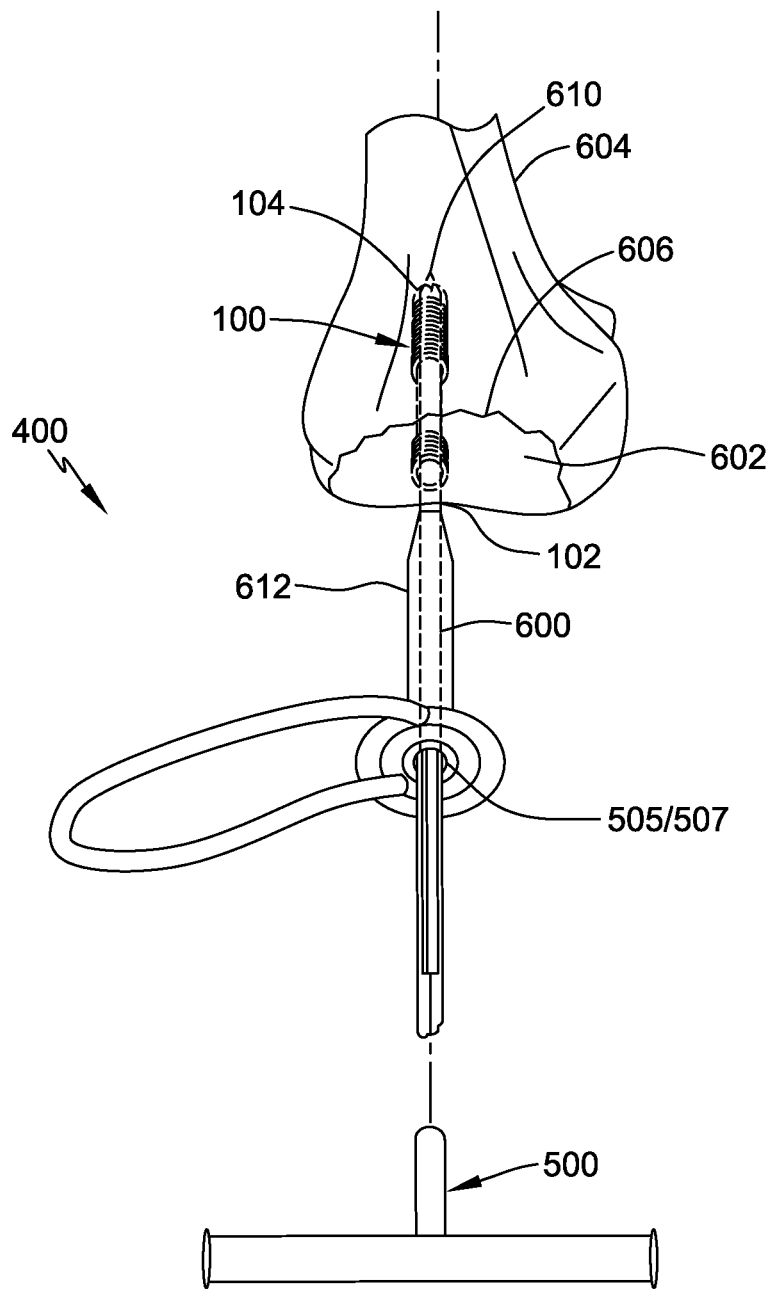
FIG. 9 is a perspective view of the cannulated screw system at the work site illustrating the cannulated screw coupling the two portions of bone.

FIG. 8 is a perspective view of a portion of cannulated screw system 400 at a work site illustrating insertion of a guide wire 600 into a first bone portion 602 and a second bone portion 604 that are separated by a bone fracture 606. FIG. 9 is a perspective view of cannulated screw system 400 at the work site illustrating cannulated screw 100 coupling bone portions 602 and 604. In operation, bone fracture 606 is to be repaired using at least one reinforced cannulated screw assembly 300 (shown in FIG. 6). The surgeon makes an incision, and advances a drill sleeve 608 or drill sleeve assembly through the soft tissue to the bone surface of first bone portion 602 contacting as shown. Guide wire 600 is then inserted through drill sleeve 608 to the desired depth and position such that a guide wire tip 610 extends through both first and second bone portions 602 and 604 that are to be joined. The position of guide wire 600 may be checked by removing drill sleeve 608 and/or by x-ray. Depending upon how many screw assemblies 300 are to be used, the same or similar procedures may be followed at the other locations as appropriate.

In the exemplary embodiment, the surgeon uses a cannulated drill bit (not shown) to drill a pilot hole for screw assembly 300 a desired length into bone portions 602 and 604. Alternatively, screw 100 is a self-tapping screw that does not require a pilot hole. However, in embodiments where screw 100 is self-tapping, it may still be helpful to drill through the bone cortex. If screw 100 is to be countersunk, e.g., to avoid soft tissue being irritated by screw head 102, then a cannulated countersink tool (not shown) may be used.

Drill sleeve 608 is then replaced by a protection sleeve 612, and a measuring device (not shown) may be used to measure the depth of the drilled hole to determine the required length of screw 100. Screw 100 is then threaded onto guide wire 600, as shown in FIG. 9, and inserted through protection sleeve 612. Torque tool 500 having first engaging portion 506 is then inserted into channel 114 (shown in FIG. 2), such that flanges 510 (shown in FIG. 7) engage axial grooves 128 (shown in FIG. 2) of screw 100. The surgeon applies torque to tool 500 to rotate screw 100 into bone portions 602 and 604 until screw tip 104 meets guide wire tip 610.

Guide wire 600 may then be removed from bone portions 602 and 604 to enable reinforcing rod 200 to be inserted into screw 100, as shown in FIG. 6. In the exemplary embodiment, the surgeon utilizes length determination features 208 (shown in FIG. 4) to modify a length of rod 200 to correspond to the selected size of screw 100. Rod 200 is inserted into screw such that protrusions 216 (shown in FIG. 4) engage helical grooves 130 (shown in FIG. 2) of screw 100. In the exemplary embodiment, the first engaging portion 506 on tool 500 is replaced by a second engaging portion 507 that is configured to correspond to recess 214 in rod 200. Alternatively, a different tool with engaging portion 507 may be used. The surgeon then engages recess 214 (shown in FIG. 5) with engaging portion 507 and applies torque to tool 500 to rotate rod 200 and cause rod to seat into screw 100. As such, when rod 200 is fully and properly seated within screw 100, rod 200 reinforces screw 100 such that the strength of screw 100 is increased comparable to that of a solid core screw. In embodiments where screw 100 and/or rod 200 require removal, the surgeon simply uses engaging portions 506 and 507 to rotate screw 100 and/or rod 200 in a direction opposite of the threading direction. As such, screw assembly 300 provides a reinforced cannulated screw that joins two bone portions and enables easy removal with a reduced risk of stripping. Alternatively, screw assembly 300 may be used in any type of surgical procedure and is not limited to only joining two bone portions.

The above described reinforced cannulated screw assemblies and systems facilitate efficient methods of reinforcing a cannulated screw. Specifically, in contrast to many known cannulated screw assemblies, the cannulated screw assemblies described herein include a cannulated screw having a channel formed therethrough that is defined by an inner wall. The inner wall includes a set of axial groves and a set of helical grooves formed therein. The axial grooves are configured to be engaged by a torque tool to drive the cannulated screw into a bone. The cannulated screw assemblies described herein also include a reinforcing rod configured for insertion into the screw channel. The reinforcing rod includes a set of protrusions that engage the helical grooves such that the protrusions are configured to move along the helical grooves and advance the reinforcing rod into the cannulated screw. As such, the reinforcing rod provides addition strength to the cannulated screw such that the cannulated screw assembly has comparable strength to a solid core screw.

The interaction of the rod protrusions and the helical grooves between the cannulated screw and the reinforcing rod reduces the chances of stripping the coupling mechanism or slipping. Additionally, the different methods of advancing the torque tool and the reinforcing rod into the cannulated screw further reduce the chances of stripping or slipping when inserting or removing the cannulated screw and/or reinforcing rod.

Exemplary embodiments of methods, systems, and apparatus for using a reinforced cannulated screw assembly are not limited to the specific embodiments described herein, but rather, components of systems and steps of the methods may be utilized independently and separately from other components and steps described herein. For example, the reinforced cannulated screw assembly may be used in combination with other application environments and in other surgical procedures, and is not limited to practice with only the bone joining surgical system and methods as described herein. Rather, the exemplary embodiment can be implemented and utilized in connection with many other applications, equipment, and systems that may benefit from the advantages described herein.

Although specific features of various embodiments of the disclosure may be shown in some drawings and not in others, this is for convenience only. In accordance with the principles of the disclosure, any feature of a drawing may be referenced and claimed in combination with any feature of any other drawing.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A reinforced cannulated screw assembly comprising:
    a cannulated screw comprising an inner wall defining a channel therethrough, the channel extending along a longitudinal axis of the cannulated screw, said inner wall comprising:
        a set of axial grooves formed therein extending in a radial direction only partially into the inner wall and extending in an axial direction substantially parallel to the channel and substantially straight;
        a set of helical grooves formed therein and spirally wound around the channel, wherein the set of axial grooves extend a first radial depth into the inner wall and the set of helical grooves extend a maximum second radial depth into said inner wall that is deeper than the first radial depth; and
    a reinforcing rod configured for insertion into the channel, said reinforcing rod comprising a pair of protrusions positioned diametrically opposite each other on the reinforcing rod, wherein each protrusion is configured to engage a helical grooves of the set of helical grooves.

2. The reinforced cannulated screw assembly in accordance with claim 1, wherein set of helical grooves includes a pair of symmetrical grooves.

3. The reinforced cannulated screw assembly in accordance with claim 1, wherein the set of axial grooves and the set of helical grooves intersect each other at least once over a predetermined length.

4. The reinforced cannulated screw assembly in accordance with claim 1, wherein the set of axial grooves extend a first axial length of said cannulated screw and the set of helical grooves extend a second axial length of said cannulated screw that is shorter than the first axial length.

5. The reinforced cannulated screw assembly in accordance with claim 1, wherein the pair of protrusions are configured to engage the set of helical grooves to facilitate insertion of said reinforcing rod into said cannulated screw.

6. The reinforced cannulated screw assembly in accordance with claim 1, wherein said reinforcing rod comprises a plurality of length determination features configured to facilitate modifying a length of said reinforcing rod to correspond to a length of said cannulated screw.

7. The reinforced cannulated screw assembly in accordance with claim 1, wherein the set of axial grooves at least partially overlaps with the set of helical grooves.

8. The reinforced cannulated screw assembly in accordance with claim 1, wherein the set of axial grooves includes a first axial end along the inner wall, and wherein the set of helical grooves includes a second axial end along the inner wall, wherein the first axial end and the second axial end are aligned along the inner wall.

9. A reinforced cannulated screw system comprising:
    a reinforced cannulated screw assembly comprising:
        a cannulated screw comprising an inner wall defining a channel therethrough, the channel extending along a longitudinal axis of the cannulated screw, said inner wall comprising:
            a set of axial grooves formed therein extending in a radial direction only partially into the inner wall and extending in an axial direction substantially parallel to the channel and substantially straight; and
            a set of helical grooves formed therein and spirally wound around the channel, wherein the set of axial grooves extend a first radial depth into the inner wall and the set of helical grooves extend a maximum second radial depth into said inner wall that is deeper than the first radial depth;
        a reinforcing rod configured for insertion into the channel, said reinforcing rod comprising a pair of protrusions positioned diametrically opposite each other on the reinforcing rod, wherein each protrusion is configured to engage a helical grooves of the set of helical grooves; and
    a torque tool configured to engage at least one of said cannulated screw and said reinforcing rod to facilitate insertion of said reinforced cannulated screw assembly into a substrate.

10. The reinforced cannulated screw system in accordance with claim 9, wherein said torque tool comprises a first engaging portion configured to engage the set of axial grooves.

11. The reinforced cannulated screw system in accordance with claim 9, wherein said pair of protrusions are configured to engage the set of helical grooves to facilitate insertion of said reinforcing rod into said cannulated screw.

12. The reinforced cannulated screw system in accordance with claim 9, wherein said reinforcing rod comprises a plurality of length determination features configured to facilitate modifying a length of said reinforcing rod to correspond to a length of said cannulated screw.

* * * * *